United States Patent [19]

Hampson et al.

[11] 4,434,087
[45] Feb. 28, 1984

[54] DETERGENT COMPOSITIONS CONTAINING SULPHOSUCCINATE MIXTURES

[75] Inventors: Jeffrey D. Hampson; Reginald Billington, both of Merseyside, England

[73] Assignee: Lever Brothers Company, New York, N.Y.

[21] Appl. No.: 400,795

[22] Filed: Jul. 22, 1982

[30] Foreign Application Priority Data

Jul. 24, 1981 [GB] United Kingdom ................. 8122975

[51] Int. Cl.$^3$ ........................... C11D 1/83; C11D 1/12
[52] U.S. Cl. .................................... 252/545; 252/547; 252/548; 252/550; 252/551; 252/552; 252/554; 252/555; 252/557; 252/558; 252/DIG. 14
[58] Field of Search ............... 252/538, 557, DIG. 13, 252/DIG. 14, 551, 553, 550, 552, 554, 555, 558, 547, 548, 545; 560/151

[56] References Cited

U.S. PATENT DOCUMENTS

| | | | |
|---|---|---|---|
| 2,028,091 | 1/1936 | Jaeger | 560/151 |
| 2,342,150 | 2/1944 | Kleinicke | 252/354 |
| 2,702,818 | 2/1955 | Jaquay | 560/2 |
| 2,813,078 | 11/1957 | Vitalis | 252/557 |
| 2,969,332 | 1/1961 | Lawler et al. | 252/354 |
| 3,206,408 | 9/1965 | Vitalis et al. | 252/557 |
| 3,301,328 | 1/1967 | Campion | 166/305 R |
| 3,629,127 | 12/1971 | Palmer et al. | 252/557 |
| 4,072,632 | 2/1978 | Reed | 252/541 |

FOREIGN PATENT DOCUMENTS

1429637 3/1976 United Kingdom .
1524448 9/1978 United Kingdom .

*Primary Examiner*—P. E. Willis, Jr.
*Attorney, Agent, or Firm*—Milton L. Honig; James J. Farrell

[57] ABSTRACT

A detergent composition with especially good foaming properties includes a di(C$_8$ alkyl) sulphosuccinate, a di(C$_6$ alkyl) sulphosuccinate and a further detergent-active agent which is preferably selected from alkyl ether sulphates, nonionic detergents and mixtures thereof. The detergent composition is preferably in liquid form and is suitable inter alia for shampoos, fabric washing and, in particular, manual dishwashing.

13 Claims, No Drawings

DETERGENT COMPOSITIONS CONTAINING SULPHOSUCCINATE MIXTURES

The present invention relates to certain detergent-active materials, and to their use in detergent compositions suitable for many purposes, for example, fabric washing products, general purpose domestic and industrial cleaning compositions, carpet shampoos, car wash products, personal washing products, shampoos, foam bath products and, above all, compositions for use in manual dishwashing operations in both hard and soft water.

The term "dishes" as used herein means any utensils involved in food preparation or consumption which may be required to be washed to free them from food particles and other food residues, greases, proteins, starches, gums, dyes, oils and burnt organic residues.

Light-duty liquid detergent compositions such as are suitable for use in washing dishes are well known. Most of the formulations in commercial use at the present time are based on anionic synthetic detergents with or without a nonionic detergent. Many of such formulations contain a sulphonate-type anionic detergent, for example, an alkylbenzene sulphonate or an alkane sulphonate, in conjunction with a sulphate-type anionic detergent, for example, an alkyl sulphate or an alkyl ether sulphate, or a nonionic detergent, for example, an alcohol ethoxylate, an alkyl phenol ethoxylate, a mono- or diethanolamide or an amine oxide. The sulphonate material generally predominates.

Alkylbenzene sulphonates and alkane sulphonates are produced by sulphonation of petrochemically derived hydrocarbons and consist of a mixture of materials of different chain lengths and sulphonate group substitution, only some of which contribute to the cleaning and foaming performance of the product, different materials being useful at different water hardnesses. The chemistry of manufacture of these materials allows at best limited control of the isomer distribution in the product alkylbenzene sulphonates and secondary alkane sulphonates.

GB No. 1,429,637 (Unilever) discloses hand dishwashing compositions containing as detergent-active material a water-soluble salt of a di($C_7$-$C_9$)alkyl ester of sulphosuccinic acid, in combination with an alkyl sulphate or an alkyl ether sulphate. These compositions show good foaming and cleaning properties which are sharply dependent on the chain length of the dialkyl sulphosuccinates, the di(n-$C_6$) and di(n-$C_{10}$) compounds giving very poor results compared with the di($C_7$-$C_9$) compounds.

It has now surprisingly been found that combinations of di($C_8$ alkyl) sulphosuccinate with the shorter chain di($C_6$ alkyl) sulphosuccinate show unexpectedly good foaming and cleaning performance, despite the poor foaming performance of the latter material itself.

These combinations of sulphosuccinates may be used together with other detergent-active agents as specified below, to form the basis of highly efficient detergent compositions, especially liquid detergent compositions, which are suitable inter alia for hand dishwashing.

U.S. Pat. No. 3,301,328 (Esso/Campion) discloses a mixture of surface active agents for use in oil-well stimulation. The mixture consists of 50-70% by volume of a di($C_8$ alkyl or alkenyl) sulphosuccinate alkali metal salt, 20-40% by volume of a di($C_6$ alkyl or alkenyl) sulphosuccinate alkali metal salt, and 5 to 20% by volume of a nonionic surfactant of the formula:

$$R(C_6H_4)_yO(CH_2CH_2O)_zCH_2CH_2OH$$

wherein R is an aliphatic group containing x carbon atoms, x is an integer from 7 to 21, y is 0 or 1, z is an integer from 6 to 28, and x and z are related by the equation:

$$0.475x - 0.33(z+1) = 0.4 \text{ to } 1.4$$

The three components are exemplified by di(n-octyl) and di(n-hexyl) sulphosuccinates and iso-octylphenol 9-10 EO.

The present invention provides a detergent composition, more especially a liquid detergent composition, comprising (a) a di($C_8$ alkyl) sulphosuccinate;
(b) a di($C_6$ alkyl) sulphosuccinate; and
(c) one or more anionic non-sulphosuccinate detergent-active agents, and/or one or more nonionic detergent-active agents other than an ethoxylated alcohol or alkyl phenol of the formula:

$$R(C_6H_4)_yO(CH_2CH_2O)_zCH_2CH_2OH$$

wherein R is an aliphatic group containing x carbon atoms wherein x is 7 to 21, y is 0 or 1, z is an integer from 6 to 28, and x and z are related by the equation:

$$0.475x - 0.33(z+1) = 0.4 \text{ to } 1.4;$$

all anionic surfactants being present in the form of salts of solubilising cations.

The component (c) is preferably selected from alkylbenzene sulphonates; secondary alkane sulphonates; alkyl ether sulphates; primary and secondary alkyl sulphates; alpha-olefin sulphonates; alkyl glyceryl ether sulphonates; fatty acid ester sulphonates; ethoxylated alcohols and alkyl phenols other than those specifically excluded above; propoxylated alcohols and alkyl phenols; amine oxides; betaines; sulphobetaines; and fatty acid mono- and di-lower-alkanolamides.

The dialkyl sulphosuccinates (a) and (b) are compounds of the formula I:

$$\begin{array}{c} CH_2\text{---}CH\text{---}SO_3X \\ | \quad\quad | \\ COOR_1 \quad COOR_2 \end{array} \quad (I)$$

wherein the R groups represent alkyl groups having 6 or 8 carbon atoms, and X represents a solubilising cation.

By "solubilising cation" is meant any cation yielding a salt of the formula I or II sufficiently soluble to be detergent active. The solubilising cation X will generally be monovalent, for example, alkali metal, especially sodium; ammonium; or substituted ammonium, for example, ethanolamine. However, certain divalent cations, notably magnesium, are also suitable.

The proportions of the two sulphosuccinate components (a) and (b) in the detergent composition of the invention are not critical. In principle the mole ratio of (a) to (b) can range from 99:1 to 1:99, preferably from 10:1 to 1:10; (a):(b) ratios of 2:1 to 1:2 give especially good all-round performance in both hard and soft water.

The $C_6$ and $C_8$ alkyl groups in the compounds (a) and (b) may be straight-chain or branched-chain. Compounds in which at least one of these groups is a straight-chain alkyl group are especially preferred. Mixtures of straight-chain and branched-chain material may if desired be used.

The di($C_8$ alkyl) sulphosuccinates are already known to be high-foaming detergent-active agents under certain conditions but may buffer from one deficiency in this respect: relatively poor performance in water of hardness greater than about 16° H. (French). Surprisingly, however, the performance of those materials in both hard and soft water, but particularly in hard water, has been found to be enhanced, according to the invention, by the admixture of the di($C_6$ alkyl) material, although the latter is not in itself a high-foaming material Advantageously the detergent compositions of the invention may also contain the unsymmetrical $C_6$ alkyl/$C_8$ alkyl sulphosuccinate. This material is described and claimed in our copending application of even date (Case C.1305) and is itself a high-foaming detergent-active agent.

The di$C_8$ and di$C_6$ compounds used according to the present invention may be prepared by any suitable method. The synthesis of dialkyl sulphosuccinates is well documented in the literature; see, for example, U.S. Pat. No. 2,028,091 (American Cyanamid).

According to a preferred method, maleic anhydride (or maleic acid or fumaric acid, but preferably maleic anhydride) is esterified with an appropriate alkanol, in the presence of an acid catalyst such as p-toluene sulphonic acid, to give the corresponding dialkyl maleate/fumarate, which is then subjected to bisulphite addition to give the dialkyl sulphosuccinate:

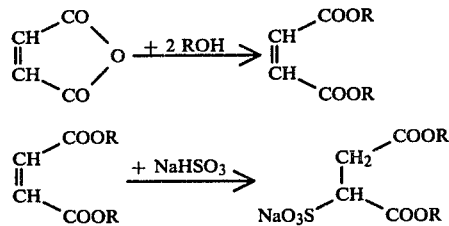

Esterification of maleic anhydride (or maleic acid or fumaric acid) with a single alcohol gives a single product in which both alkyl groups are the same. Thus di$C_8$ sulphosuccinate may be prepared from octanol, and di$C_6$ sulphosuccinate from hexanol.

about 50 mole percent of the unsymmetrical diester (isomer mixture).

If one of the starting alcohols is an octanol and the other a hexonal, the mixture of di$C_8$, $C_6$/$C_8$ and di$C_6$ sulphosuccinates obtained may with advantage be used in the detergent compositions of the present invention.

Thus, according to a further preferred embodiment of the invention, the di$C_8$/di$C_6$ sulphosuccinate mixture is obtained by a process which includes the esterification of a suitable starting material, especially maleic anhydride but also maleic acid, fumaric acid or sulphosuccinic acid, with a mixture of a $C_8$ alkanol and a $C_6$ alkanol.

The foaming performance of the detergent compositions of the invention is generally substantially better than would be expected from the performance of the individual components.

As indicated previously, dialkyl sulphosuccinates may be manufactured from alkanols, which are commercially available as materials of strictly defined chain length: thus the chain length of the sulphosuccinates may be precisely controlled.

As well as the two specified sulphosuccinate components, the detergent compositions of the invention also contain as an essential component at least one further, non-sulphosuccinate, detergent-active material which may be anionic or nonionic. This material is preferably selected from the list given previously.

In a preferred embodiment of the invention, this component (c) is selected from the group consisting of alkyl ether sulphates, nonionic detergents other than those specifically excluded above, and mixtures thereof.

Preferred alkyl ether sulphates are primary and secondary alcohol ethoxy sulphates represented by the general formula $R_1$—O—$(C_2H_4O)_n$—$SO_3M$, in which $R_1$ represents an alkyl group having 10 to 18 carbon atoms, the degree of ethoxylation n is from 1 to 12, and M represents an alkali metal, an ammonium or an amine cation. The $R_1$ group more preferably contains 10 to 15 carbon atoms, and n is more preferably from 1 to 8. In any commercially available ether sulphate, there will of course be a spread of degree of ethoxylation, and n will represent an average value. An example of a suitable amine cation M is the monoethanolamine cation.

Preferred nonionic detergents are in particular the condensates of straight or branched chain primary or secondary aliphatic alcohols with ethylene oxide, of the general formula $R_2$—O—$(C_2H_4O)_mH$, in which $R_2$ is an alkyl group having from 8 to 20 carbon atoms; m, the average degree of ethoxylation, ranges from 5 to 20; and

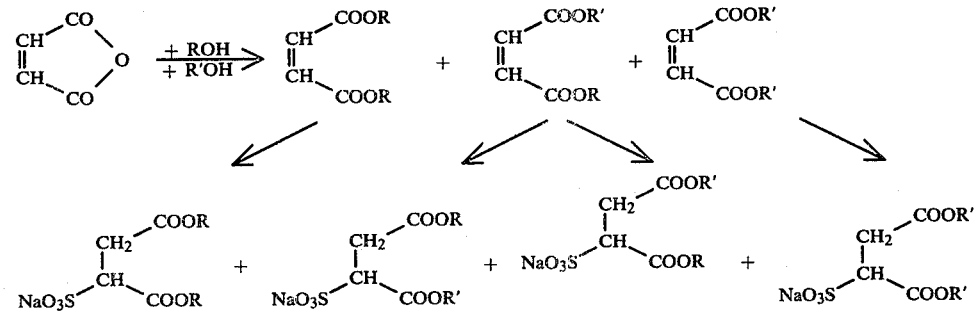

If a substantially equimolar mixture of the two starting alcohols is used, statistically one would expect about 25 mole percent each of the two symmetrical diesters and the relationship between the number of carbon atoms in the alkyl group $R_2$ and the degree of ethoxylation m is not as specified above.

If $r_2$ is the number of carbon atoms in the group $R_2$, $r_2$ and $m$ preferably satisfy the following equation:

$$0.475r_2 - 0.33m = 1.45 \text{ to } 3.00$$

$r_2$ is advantageously from 8 to 12.

Other suitable nonionic detergents include nonionic alkylphenol polyethers of the general formula $R_3$—$C_6H_4$—$O$—$(C_2H_4O)_pH$, where $R_3$ is an alkyl group having from 6 to 16 carbon atoms, preferably 8 to 12 carbon atoms, and the average degree of ethoxylation $p$ is from 8 to 16, preferably 9 to 12, and the relationship between the number of carbon atoms $r_3$ in the group $R_3$ and the degree of ethoxylation $p$ is not as specified above. $r_3$ and $p$ preferably satisfy the following equation:

$$0.475r_3 - 0.33p = (-0.60) \text{ to } 0.35$$

$r_3$ is advantageously from 8 to 12.

A third group of nonionic detergents of interest for use in the present invention is comprised by the nonionic condensates of fatty acids and ethylene oxide of the general formula $R_4$—$CO$—$O$—$(C_2H_4O)_qH$, where $R_4$ is an alkyl group having from 12 to 18 carbon atoms, and the average degree of ethoxylation $q$ is from 8 to 16.

Yet another class of nonionic detergent of especial interest for use in the present invention is comprised by the $C_{12}$–$C_{14}$ alkyl mono- and di-lower-alkanolamides, especially the mono- and diethanolamides. Coconut and lauric mono- and diethanolamides are preferred.

Amine oxides are also of interest, in particular those containing one $C_{10}$–$C_{28}$ alkyl chain and two $C_1$–$C_4$ alkyl or hydroxyalkyl groups.

Other materials outside the especially preferred group of alkyl ether sulphates and nonionic detergents which are nevertheless of interest for use as part or whole of component (c) include linear $C_{10}$–$C_{13}$ alkylbenzene sulphonates; secondary alkane sulphonates; and primary and secondary alkyl sulphates. All these combinations are highly suitable for hand dishwashing compositions, and some will of course also be suitable for other types of product.

The weight ratio of the sulphosuccinate components (a) and (b) to the non-sulphosuccinate component (c) is preferably within the range of from 1:4 to 20:1, more preferably from 1:1 to 12:1.

If other dialkyl sulphosuccinates, for example the $C_6/C_8$ material mentioned above, are present, the ratio of total sulphosuccinate to component (c) is preferably as specified in the previous paragraph.

Detergent compositions according to the invention may if desired contain other detergent-active agents as well as the specified sulphosuccinate-containing mixture of the invention. These may, for example, be cationic, amphoteric or zwitterionic. The type of detergent-active material present in addition to the sulphosuccinate mixture of the invention will depend on the intended end-use of the product.

As previously mentioned, the detergent compositions of the invention are preferably liquids, although the $diC_6$ and $diC_8$ sulphosuccinates are themselves solids at ambient temperature. The detergent compositions of the invention may, however, be in any suitable physical form, for example, powders, solid bars or gels. They may be used for any type of detergent product, for example, fabric washing products, general purpose domestic and industrial cleaning compositions, carpet shampoos, car wash products, personal washing products, shampoos, foam bath products, and mechanical and manual dishwashing compositions.

The sulphosuccinate-based compositions with which the invention is concerned are however outstandingly suitable for incorporation in liquid products. These liquid detergent products may be used for all normal detergent purposes, but are of especial interest for use as fabric washing liquids, both built and unbuilt, for both heavy-duty laundry and for washing delicate fabrics; as shampoo; and, above all, as products for dishwashing, especially for hand dishwashing. These liquid products may range from concentrates, containing virtually 100% active detergent, to the more dilute aqueous solutions seen by the consumer. In the latter type of product the total amount of detergent-active material will generally range from 2 to 60% by weight, the balance being made up by water; minor ingredients such as perfume, colour, preservatives, germicides and the like; and, if necessary, a viscosity and solubility control system, referred to in the art as a hydrotrope. The hydrotrope system, for example, may comprise any one or more of the following materials: lower alcohols, especially ethanol; urea; and lower mono- or dialkylbenzene sulphonates, such as sodium or ammonium xylene sulphonates or toluene sulphonates.

The invention is further illustrated by the following non-limiting Examples.

EXAMPLE 1

Preparation of Statistical Mixture of $C_6/C_8$ Sulphosuccinates

Maleic anhydride (98 g, 1 mole) in toluene (400 ml) containing octan-1-ol (130 g, 1.0 mole) and hexan-1-ol (120 g, 1.0 mole) and p-toluene sulphonic acid (2 g) was stirred under reflux for 3 hours. Water was removed azeotropically by means of a Dean & Stark apparatus (approximately 18 ml, i.e. 1 mole, of water were collected). The crude reaction mixture was cooled and washed with 30% sodium hydroxide solution, then water, then brine, before drying over anhydrous magnesium sulphate. The mixture was filtered and the solvents removed in vacuo to yield an oil (293 g). This oil was shown by gas-liquid chromatography to consist of the symmetrical $diC_8$ diester, the unsymmetrical $C_6/C_8$ diester and the symmetrical $diC_6$ diester in molar proportions of approximately 1:2:1.

The oil prepared as above without further purification, was dissolved in industrial methylated spirit (500 ml) and refluxed with 475 ml of a 40% aqueous solution of sodium metabisulphite for 6 hours. The solvent was removed in vacuo to yield a crude solid which was taken up in hot ethanol, filtered hot, and allowed to crystallise at 0° C. A yield of 300 g was obtained, consisting of about 98% detergent-active material and about 0.10–0.15% non-detergent organic matter. By high-performance liquid chromatography it was shown to consist of the $diC_8$, $C_6/C_8$ and $diC_6$ dialkyl sulphosuccinates in molar proportions of approximately 1:2:1.

EXAMPLES 2–10

The foaming performances of various sulphosuccinate mixtures according to the invention were measured by means of a modified Schlachter-Dierkes test based on the principle described in *Fette und Seifen* 1951, 53, 207. A 100 ml aqueous solution of each material tested, having a concentration of 0.05% active detergent, generally in 5° H. or 24° H. water (French hardness i.e. 5 or 24 parts calcium carbonate per 100,000 parts water), at 45° C., was rapidly oscillated using a vertically oscillating perforated disc within a graduated cylinder. After the initial generation of foam, increments (0.2 g) of soil (9.5 parts commercial cooking fat, 0.25 parts oleic acid, 0.25 parts stearic acid and 10 parts wheat starch in 120 parts water; in some cases, with 7 parts casein replacing 7 parts of water) were added at 15-second intervals (10 seconds' mild agitation and 5 seconds' rest) until the foam collapsed. The result was recorded as the number of soil increments (NSI score): a score difference of 6 or less is generally regarded as insignificant. Each result was typically the average of 3 or 4 runs.

EXAMPLE 2

The foaming performance of a sulphosuccinate-based mixture according to the invention was compared with that of a conventional alkylbenzene sulphonate/alkyl ether sulphate dishwashing formulation. The sulphosuccinate-based composition consisted of a mixture of the $C_6/C_8$ ternary mix (1:2:1) prepared in Example 1 and the ammonium salt of a sulphated linear $C_{12}$–$C_{15}$ primary alcohol condensed with 3 (average) ethylene oxide moieties (Dobanol (Trade Mark) 25-3A ex Shell), at a weight ratio of 4:1; and the comparison composition consisted of a mixture of a linear $C_{10}$–$C_{12}$ alkyl benzene sulphonate (Dobs (Trade Mark) 102 ex Shell) and Dobanol 25-3A at a weight ratio of 4:1. The tests were carried out with both normal and casein soil. The results are shown in Table 1.

TABLE 1

| | 5° H | | 24° H | |
|---|---|---|---|---|
| | Normal soil | Casein soil | Normal soil | Casein soil |
| Alkylbenzene sulphonate/alkyl ether sulphate | 52 | 9 | 60 | 34 |
| Sulphosuccinate mix/alkyl ether sulphate | 75 | 19 | 73 | 58 |

It will be seen that the sulphosuccinate mix is superior to the alkylbenzene sulphonate mix under all four sets of conditions.

EXAMPLE 3

The performances of compositions based on binary mixtures of di-n-octyl and di-n-hexyl sulphosuccinate at various ratios, together with alkyl ether sulphate (Dobanol 25-3A) at a 4:1 weight ratio, were compared with the performance of corresponding compositions based on the single sulphosuccinates, using normal soil only. The results were shown in Table 2.

TABLE 2

| Ratio | 5° H | | 24° H | |
|---|---|---|---|---|
| $diC_6$:$diC_8$ | Measured | (Predicted) | Measured | (Predicted) |
| $diC_8$ alone | 65 | — | 31 | — |
| 1:2 | 57 | (47) | 36 | (26) |
| 1:1 | 48 | (37) | 52 | (23) |
| 2:1 | 49 | (28) | 55 | (21) |
| $diC_6$ alone | 10 | — | 16 | — |

It will be seen that the measured score is substantially higher than the predicted score in every case. A ratio of 1:1 to 2:1 appears to be optimum for all-round performance.

EXAMPLE 4

Example 3 was repeated using a ratio of sulphosuccinate to ether sulphate of 2:1. The results are shown in Table 3.

TABLE 3

| Ratio | 5° H | | 24° H | |
|---|---|---|---|---|
| $diC_6$:$diC_8$ | Measured | (Predicted) | Measured | (Predicted) |
| $diC_8$ alone | 47 | — | 28 | — |
| 1:2 | 45 | (36) | 38 | (23) |
| 1:1 | 39 | (30) | 43 | (21) |
| 2:1 | 44 | (24) | 43 | (19) |
| $diC_6$ alone | 13 | — | 14 | — |

The overall scores are generally slightly lower, although still very good, but the same trends are observable as in Example 3.

EXAMPLE 5

Example 3 was repeated using a nonionic surfactant in place of the ether sulphate. The nonionic surfactant used was a $C_9$–$C_{11}$ straight-chain primary alcohol blend ethoxylated with an average of 8 ethylene oxide moieties (Dobanol (Trade Mark) 91-8 ex Shell). The results are shown in Table 4, and are very similar to those of Example 3.

TABLE 4

| Ratio | 5° H | | 24° H | |
|---|---|---|---|---|
| $diC_6$:$diC_8$ | Measured | (Predicted) | Measured | (Predicted) |
| $diC_8$ alone | 60 | — | 28 | 13 |
| 1:2 | 57 | (40) | 43 | (19) |
| 1:1 | 62 | (30) | 47 | (15) |
| 2:1 | 54 | (21) | 50 | (11) |
| $diC_6$ alone | 1 | — | 2 | — |

EXAMPLE 6

Example 5 was repeated using a sulphosuccinate to nonionic surfactant ratio of 2:1 instead of 4:1. The results are shown in Table 5. Again excellent performance, substantially higher than predicted, was obtained in each case.

TABLE 5

| Ratio | 5° H | | 24° H | |
|---|---|---|---|---|
| $diC_6$:$diC_8$ | Measured | (Predicted) | Measured | (Predicted) |
| $diC_8$ alone | 53 | — | 32 | — |
| 1:2 | 55 | (37) | 49 | (22) |
| 1:1 | 54 | (28) | 51 | (17) |
| 2:1 | 53 | (20) | 52 | (13) |
| $diC_6$ alone | 4 | — | 3 | — |

EXAMPLE 7

Example 3 was repeated using, at a sulphosuccinate to cosurfactant ratio of 4:1, a mixed cosurfactant consisting of a 1:1 mixture of the ether sulphate of Example 3 and the nonionic surfactant of Example 5. The results are shown in Table 6 and again all three compositions according to the invention displayed excellent performance at both water hardnesses.

TABLE 6

| Ratio | 5° H | | 24° H | |
|---|---|---|---|---|
| $diC_6$:$diC_8$ | Measured | (Predicted) | Measured | (Predicted) |
| $diC_8$ alone | 71 | — | 35 | — |
| 1:2 | 59 | (49) | 48 | (26) |
| 1:1 | 59 | (37) | 52 | (21) |

TABLE 6-continued

| Ratio | 5° H | | 24° H | |
|---|---|---|---|---|
| $diC_6$:$diC_8$ | Measured | (Predicted) | Measured | (Predicted) |
| 2:1 | 58 | (26) | 52 | (17) |
| $diC_6$ alone | 4 | — | 8 | — |

EXAMPLE 8

Example 7 was repeated at a sulphosuccinate to co-surfactant ratio of 2:1. The results are shown in Table 7 and again the scores were excellent at both water hardnesses and substantially higher than the predicted scores.

TABLE 7

| Ratio | 5° H | | 24° H | |
|---|---|---|---|---|
| $diC_6$:$diC_8$ | Measured | (Predicted) | Measured | (Predicted) |
| $diC_8$ alone | 66 | — | 33 | — |
| 1:2 | 57 | (46) | 42 | (26) |
| 1:1 | 58 | (36) | 48 | (22) |
| 2:1 | 48 | (27) | 45 | (19) |
| $diC_8$ alone | 7 | — | 12 | — |

EXAMPLE 9

The statistical mixture prepared in Example 1 was mixed with the ether sulphate used in Example 2 in a weight ratio of 4:1, and the foaming performance of this mixture was compared with those of corresponding mixtures of the individual sulphosuccinates with the ether sulphate at the same mole ratio of 4:1. For this comparison the $C_6/C_8$ compound was prepared as described in Example 4 of our copending application of even date (Case C.1304).

The results are shown in Table 8.

TABLE 8

| Sulphosuccinate material | 5° H | 24° H |
|---|---|---|
| $diC_8$ | 48 | 23 |
| $diC_6$ | 12 | 15 |
| $C_6/C_8$ | 48 | 87 |
| Mixture: | | |
| measured | 75 | 73 |
| (predicted) | (39) | (53) |

EXAMPLE 10

In this experiment the effect of varying the ratio of sulphosuccinate mixture to ether sulphate over a wider range was investigated. The sulphosuccinate mixture was the $C_6/C_8$ ternary mixture (1:2:1) and the ether sulphate was again Dobanol 25-3A. The results are shown in Table 9.

Good scores were obtained at all ratios, those at ratios of 1:1, 2:1 and 4:1 being especially outstanding and significantly higher than the predicted scores.

TABLE 9

| Material/ | 5° H | | 24° H | |
|---|---|---|---|---|
| weight ratio | Measured | (Predicted) | Measured | (Predicted) |
| Sulphosuccinate alone | 61 | — | 49 | — |
| 20:1 | 87 | (59) | 59 | (48) |
| 12:1 | 88 | (59) | 57 | (48) |
| 8:1 | 81 | (58) | 61 | (47) |
| 4:1 | 75 | (55) | 73 | (46) |
| 2:1 | 69 | (51) | 93 | (43) |
| 1:1 | 53 | (45) | 93 | (40) |
| 1:2 | 43 | (40) | 58 | (38) |

TABLE 9-continued

| Material/ | 5° H | | 24° H | |
|---|---|---|---|---|
| weight ratio | Measured | (Predicted) | Measured | (Predicted) |
| 1:4 | 36 | (36) | 44 | (35) |
| Ether sulphate alone | 30 | — | 32 | — |

EXAMPLE 11

In this experiment the dishwashing performance of a dialkyl sulphosuccinate/alkyl ether sulphate mixture was compared with that of an alkyl benzene sulphonate/alkyl ether sulphate mixture using a plate washing test.

In the test, plates soiled with a starch/fat/fatty acid mixture were washed in a standard manner with 5 liters of test solution (total concentration 0.4 g/liter in 5° H. or 24° H. water) in a bowl, until only a third of the surface of the solution in the bowl was covered with foam. The number of plates washed before this arbitrary end-point was reached was taken as an indicator of dishwashing performance.

The composition according to the invention to be used in this test was a 4:1 by weight mixture of the statistical mixture prepared in Example 1 and the alkyl ether sulphate (Dobanol 25-3A) used in Example 2; and the comparison composition was a 4:1 by weight mixture of the alkylbenzene sulphonate (Dobs 102) used in Example 2 and the alkyl ether sulphate (Dobanol 25-3A) used in Example 2. The results, which clearly show the superiority of the sulphosuccinate-based composition, are shown in Table 10.

TABLE 10

| | Number of Plates Washed | |
|---|---|---|
| | 5° H | 24° H |
| Sulphosuccinate/alkyl ether sulphate | 51 | 54 |
| Alkylbenzene sulphonate/alkyl ether sulphate | 33 | 28 |

EXAMPLE 12

In this experiment the dishwashing performance of a series of dilute solutions of the statistical mixture prepared in Example 1 was evaluated using a slightly different plate washing test method.

In this test, the plates used were soiled with a corn oil/oleic acid/stearic acid/rice starch soil, and each was prewetted with 7 ml of 5°H water. A sponge was dipped into a 4% solution (in 5°H water) of the test product and used to wash the plates using a set procedure, the number of plates washed before foam collapse occurred being taken as an indicator of dishwashing performance.

The products according to the invention used for this test were dilute aqueous solution of a 4:1 by weight mixture of the statistical mixture of Example 1 with the ether sulphate used in Example 2 (Dobanol 25-3A). The comparison products were dilute aqueous solutions of a 4:1 by weight mixture of a $C_{11}$–$C_{14}$ linear alkylbenzene sulphonate (ex Mitsubishi, Japan) and a $C_{11}$–$C_{13}$ oxo alcohol 3EO sulphate (Synperonic (Trade Mark) 3S-60 ex ICI). The test results are shown in Table 11.

From these results it may be inferred that the sulphosuccinate-based system at a concentration of about 5.5% by weight would have a performance equivalent to that of the alkylbenzene sulphonate-based system at 15%.

TABLE 11

| Total Concentration (by weight %) | Number of Plates Washed | |
|---|---|---|
| | Sulphosuccinate Mix | Alkylbenzene Sulphonate Mix |
| 15 | (not tested) | 17 |
| 7.5 | 24 | 10 |
| 3.75 | 14 | 7 |

EXAMPLE 13

The efficacy of a sulphosuccinate mix according to the invention as a shampoo detergent was investigated in the following experiment, in which the foaming capacity of the mix in the presence of simulated sebum was compared with those of some known shampoo detergents. The sulphosuccinate mix used was the $C_6/C_8$ statistical mixture prepared in Example 1, and the simulated sebum had the following composition:

| | Weight % |
|---|---|
| Triolein | 35.0 |
| Tristearin | 10.0 |
| Oleic acid | 10.0 |
| Stearic acid | 5.0 |
| Squalene | 35.0 |
| Cholesterol | 5.0 |

For each material tested, a 12% solution in 14°H water was prepared (this simulates a typical shampoo composition in the bottle) and was then diluted by a factor of 9 (this simulates the dilution of a shampoo by the consumer immediately before and during application to the hair). 1 g of artificial sebum was added to a fixed volume (180 ml) of each diluted (1.33%) solution, mechanical agitation was effected using a food mixer rotating at 600 rpm, and the volume of foam generated after 2 minutes was measured. The results are shown in Table 12.

TABLE 12

| Detergent-active Material | Foam Volume (ml) |
|---|---|
| Dodecyl benzene sulphate | 40 |
| Monoalkyl sulphosuccinate (Condanol (Trade Mark) SBFA/3) | 110 |
| Sodium lauryl ether (2EO) sulphate | 130 |
| Monoethanolamine lauryl sulphate | 200 |
| Sulphosuccinate mix | 240 |

It will be seen then in this in vitro test the sulphosuccinate mix of the invention produces significantly higher volumes of foam than do the conventionnal shampoo detergents sodium lauryl ether sulphates and monoethanolamine lauryl sulphate. The monoalkyl sulphosuccinate performs substantially worse than the dialkyl sulphosuccinate mix of the invention.

EXAMPLE 14

Using the procedure of Example 13, the effect of diluting the initial solution from 12% to 6% was investigated. The results are shown in Table 13.

TABLE 13

| Detergent-active Material | Concentration of initial solution (weight %) | Foam Volume (ml) |
|---|---|---|
| $C_6/C_8$ sulphosuccinate mix | 12% | 250 |
| | 6% | 225 |
| Sodium lauryl ether sulphate | 12% | 120 |

The results show that even using half the concentration of detergent-active material in the initial solution, a result significantly better than that for the conventional material at the higher concentration is obtained.

We claim:

1. A foaming detergent composition comprising
(a) a di($C_8$ alkyl) sulphosuccinate;
(b) a di($C_6$ alkyl) sulphosuccinate; and
(c) one or more anionic non-sulphosuccinate detergent-active agents, and/or one or more nonionic detergent-active agents other than an ethoxylated alcohol or alkyl phenol of the formula:

$$R(C_6H_4)_yO(CH_2CH_2O)_z CH_2CH_2OH$$

wherein R is an aliphatic group containing x carbon atoms wherein x is 7 to 21, y is 0 or 1, z is an integer from 6 to 28, and x and z are related by the equation:

$$0.475x - 0.33(z+1) = 0.4 \text{ to } 1.4;$$

all anionic surfactants being present in the form of salts of solubilising cations; the mole ratio of sulphosuccinates (a) to (b) being within the range from 10:1 to 1:10 and the weight ratio of (a) and (b) to non-sulphosuccinate (c) being within the range of from 1:4 to 20:1.

2. The detergent composition of claim 1, wherein component (a) comprises di-n-octyl sulphosuccinate.

3. The detergent composition of claim 1, wherein component (b) comprises di-n-hexyl sulphosuccinate.

4. The detergent composition of claim 1, which further comprises about 50% of a ($C_6$ alkyl)($C_8$ alkyl) sulphosuccinate.

5. The detergent composition of claim 4, which comprises a sulphosuccinate ester mixture which is the reaction product of a mixture of hexanol and octanol with a compound selected from the group consisting of maleic anhydride, maleic acid, fumaric acid and mixtures thereof, the resultant maleate/fumarate esters being further reacted with bisulphite.

6. The detergent composition of claim 4, which comprises a sulphosuccinate ester mixture which is the reaction product of a mixture of hexanol and octanol with a sulphosuccinic acid.

7. The detergent composition of claim 1, wherein component (c) comprises one or more detergent-active agents selected from the group consisting of alkylbenzene sulphonates; secondary alkane sulphonates; alkyl ether sulphates; primary and secondary alkyl sulphates; alpha-olefin sulphonates; alkyl glyceryl ether sulphonates; fatty acid ester sulphonates; ethoxylated alcohols and alkyl phenols other than specifically excluded in claim 1; propoxylated alcohols and alkyl phenols; amine oxides; betaines; sulphobetaines; and fatty acid mono- and di-lower-alkanolamides.

8. The detergent composition of claim 7, wherein component (c) is selected from the group consisting of alkyl ether sulphates, nonionic detergents other than those specifically excluded in claim 1, and mixtures thereof.

9. The detergent composition of claim 7, wherein component (c) comprises at least one primary or secondary alcohol ethoxy sulphate of the formula $$R_1-O-(C_2H_4O)_n-SO_3M$$

wherein $R_1$ represents an alkyl group having from 10 to 18 carbon atoms and n, the average degree of ethoxylation, is from 1 to 12.

10. The detergent composition as of claim 7, wherein component (c) comprises at least one nonionic detergent of the formula:

$$R_2-O-(C_2H_4O)_mH$$

wherein $R_2$ represents an alkyl group having $r_2$ carbon atoms, $r_2$ is from 8 to 20, and m, the average degree of ethoxylation, is from 5 to 20, $r_2$ and m being related by the equation:

$$0.475r_2 - 0.33m = 1.45 \text{ to } 3.00.$$

11. The detergent composition of claim 1, which is a liquid.

12. The detergent composition of claim 11, which is in the form of an aqueous solution having a total content of detergent-active material within the range of from 2 to 60% by weight.

13. The detergent composition of claim 11, which includes a viscosity control system comprising at least one material selected from the group consisting of lower alkanols, urea, and lower alkylbenzene sulphonates.

* * * * *